(12) United States Patent
Rella et al.

(10) Patent No.: US 10,113,997 B2
(45) Date of Patent: Oct. 30, 2018

(54) METHODS FOR GAS LEAK DETECTION AND LOCALIZATION IN POPULATED AREAS USING TWO OR MORE TRACER MEASUREMENTS

(71) Applicant: Picarro, Inc., Santa Clara, CA (US)

(72) Inventors: Chris W. Rella, Sunnyvale, CA (US); Eric R. Crosson, Livermore, CA (US); Michael R. Woelk, Livermore, CA (US); Sze Meng Tan, Santa Clara, CA (US); Yonggang He, Union City, CA (US); David Steele, San Francisco, CA (US)

(73) Assignee: Picarro, Inc., Santa Clara, CA (US)

( * ) Notice: Subject to any disclaimer, the term of this patent is extended or adjusted under 35 U.S.C. 154(b) by 84 days.

(21) Appl. No.: 15/088,885

(22) Filed: Apr. 1, 2016

(65) Prior Publication Data

US 2016/0216172 A1   Jul. 28, 2016

Related U.S. Application Data

(63) Continuation-in-part of application No. 14/493,853, filed on Sep. 23, 2014, now Pat. No. 9,739,758, which
(Continued)

(51) Int. Cl.
*G01M 3/40* (2006.01)
*G01N 33/00* (2006.01)
(Continued)

(52) U.S. Cl.
CPC .......... *G01N 33/0009* (2013.01); *G01M 3/22* (2013.01); *G01M 3/38* (2013.01); *G01N 21/01* (2013.01);
(Continued)

(58) Field of Classification Search
USPC .............................................................. 73/40
See application file for complete search history.

(56) References Cited

U.S. PATENT DOCUMENTS 3,444,721 A * 5/1969 Hearn ..................... G01M 3/20
73/23.2
4,056,969 A * 11/1977 Barringer ................. G01V 5/02
250/255
(Continued)

FOREIGN PATENT DOCUMENTS

EP         2503323       9/2012
WO       WO99/42814     8/1999
(Continued)

*Primary Examiner* — Eric S McCall
*Assistant Examiner* — Mohammed E Keramet-Amircola
(74) *Attorney, Agent, or Firm* — Lumen Patent Firm (57) ABSTRACT

Improved gas leak detection from moving platforms is provided. Automatic horizontal spatial scale analysis can be performed in order to distinguish a leak from background levels of the measured gas. Source identification can be provided by using two or more tracer measurements of isotopic ratios and/or chemical tracers to distinguish gas leaks from other sources of the measured gas. Multi-point measurements combined with spatial analysis of the multi-point measurement results can provide leak source distance estimates. Qualitative source identification is provided. These methods can be practiced individually or in any combination.

18 Claims, 9 Drawing Sheets

Related U.S. Application Data is a continuation-in-part of application No. 13/656,096, filed on Oct. 19, 2012, now Pat. No. 9,618,417.

(60) Provisional application No. 61/646,487, filed on May 14, 2012, provisional application No. 61/627,915, filed on Oct. 20, 2011.

(51) Int. Cl.
*G01N 21/3504* (2014.01)
*G01M 3/38* (2006.01)
*G01N 21/01* (2006.01)
*G01N 21/39* (2006.01)
*G01M 3/22* (2006.01)
*G01N 21/03* (2006.01)

(52) U.S. Cl.
CPC ......... *G01N 21/3504* (2013.01); *G01N 21/39* (2013.01); *G01N 2021/0314* (2013.01); *G01N 2201/025* (2013.01)

(56) References Cited

U.S. PATENT DOCUMENTS

| | | | | |
|---|---|---|---|---|
| 4,164,138 A | * | 8/1979 | Burkhart | G01M 3/22 73/23.2 |
| 5,317,156 A | * | 5/1994 | Cooper | G01N 21/39 250/339.13 |
| 6,274,870 B1 | * | 8/2001 | Kubo | A61B 5/097 250/339.13 |
| 6,750,453 B1 | | 6/2004 | Nelson et al. | |
| 7,704,746 B1 | | 4/2010 | White et al. | |
| 2004/0263852 A1 | * | 12/2004 | Degtiarev | G01M 3/38 356/437 |
| 2006/0203248 A1 | * | 9/2006 | Reichardt | G01M 3/20 356/437 |
| 2007/0061114 A1 | | 3/2007 | Kalayeh | |
| 2009/0193875 A1 | * | 8/2009 | Komninos | G01J 5/02 73/40 |
| 2010/0198736 A1 | * | 8/2010 | Marino | G01N 21/3504 705/308 |
| 2011/0122397 A1 | | 5/2011 | Wong | |
| 2012/0092649 A1 | | 4/2012 | Wong | |

FOREIGN PATENT DOCUMENTS

| | | |
|---|---|---|
| WO | WO2009/134692 | 11/2009 |
| WO | WO2009/156437 | 12/2009 |
| WO | WO2012/046180 | 4/2012 |

* cited by examiner

METHODS FOR GAS LEAK DETECTION AND LOCALIZATION IN POPULATED AREAS USING TWO OR MORE TRACER MEASUREMENTS

CROSS REFERENCE TO RELATED APPLICATIONS

This application is a continuation in part of U.S. Ser. No. 14/493,853, filed on Sep. 23, 2014 and hereby incorporated by reference in its entirety. Application Ser. No. 14/493,853 is a continuation in part of U.S. Ser. No. 13/656,096, filed on Oct. 19, 2012. Application Ser. No. 13/656,096 claims the benefit of U.S. provisional patent application 61/627,915, filed on Oct. 20, 2011, entitled "Methods for gas leak detection and localization in populated areas", and hereby incorporated by reference in its entirety. Application Ser. No. 13/656,096 also claims the benefit of U.S. provisional patent application 61/646,487, filed on May 14, 2012, entitled "Gas detection systems and methods", and hereby incorporated by reference in its entirety.

FIELD OF THE INVENTION

This invention relates to gas leak detection.

BACKGROUND

Gas leak detection is an important practical problem. In many cases, it is desirable to rapidly search for gas leaks over a large region. One approach that has been considered for such applications is to mount a gas leak detection instrument on a moving vehicle, e.g., as considered in U.S. Pat. Nos. 3,107,517, 3,444,721, and 4,164,138. However, conventional approaches for mobile gas leak detection suffer from significant disadvantages. Typically, these disadvantages include one or more of: 1) difficulty in distinguishing a leak from background, 2) difficulty with distinguishing a leak from other possible sources of the measured gas, and 3) lack of an estimated distance to the leak source.

Accordingly, it would be an advance in the art to overcome these difficulties.

SUMMARY

The present approach alleviates these difficulties in the following manner. Automatic horizontal spatial scale analysis can be performed in order to distinguish a leak from background levels of the measured gas. Source identification can be provided by using isotopic ratios and/or chemical tracers to distinguish gas leaks from other sources of the measured gas. Multi-point measurements combined with spatial analysis of the multi-point measurement results can provide leak source distance estimates. Qualitative source identification is provided. These methods can be practiced individually or in any combination.

DETAILED DESCRIPTION

It is convenient to define a gas leak as being any situation where gas is present in the environment in above-background concentrations. Gas leaks as defined include, but are not limited to: leaks from gas pipes or transportation systems (e.g., natural gas leaks), leaks from gas processing or handling facilities, and emissions from gas sources into the environment (e.g., pollution, gas emission from landfills, etc.).

A gas plume model is any mathematical model that relates gas concentration to position in space.

A) Horizontal Analysis

A1) Principles

Figure 1A:
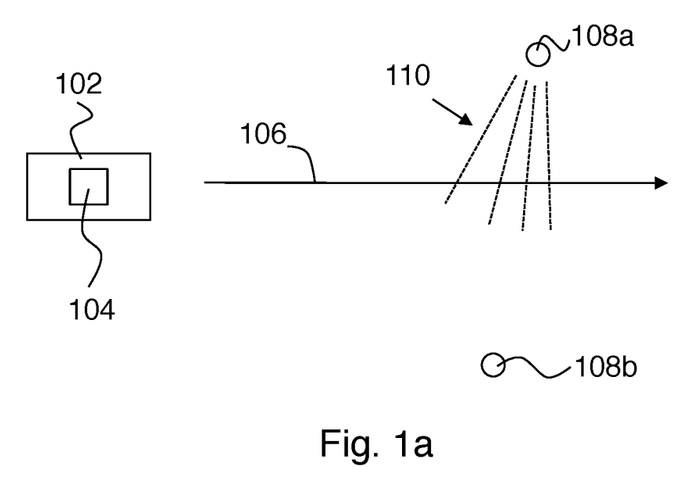
FIGS. 1a-b schematically show horizontal analysis according to embodiments of the invention.
Figure 1B:
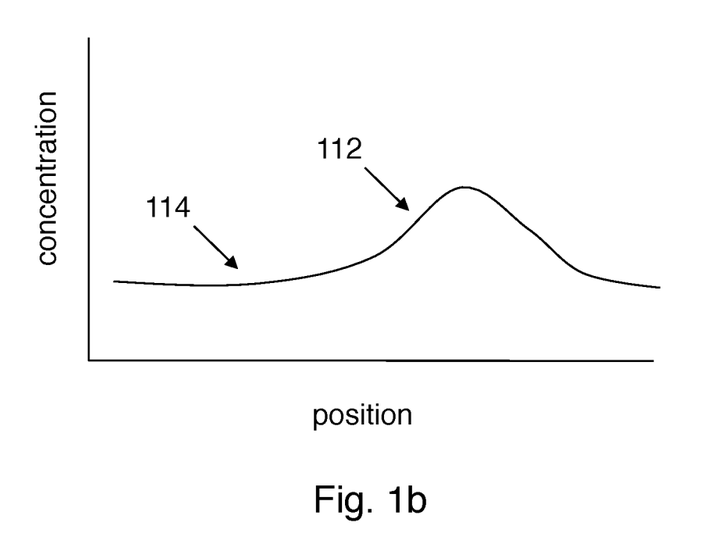

FIGS. 1a-b show an example of horizontal spatial scale analysis according to embodiments of the invention. A moving platform 102 proceeds along at least one platform track 106. Platform 102 can be any vehicle, such as a car, truck, van, or bicycle. Platform 102 can also be any other mobile entity capable of transporting the gas measurement instrument, such as a person, pack animal, etc. Platform track 106 is disposed near one or more potential gas leak locations (e.g., 108a, 108b). For simplicity, the platform track is shown as a single line segment, but in practice the platform track can be any combination of curves and line segments. In this example, a leak at location 108a emits a gas plume 110 that intersects platform track 106. A gas measurement instrument 104 is disposed on the platform. Practice of the invention does not depend critically on details of the gas inlet to instrument 104. One implementation is to place this inlet at the front of the platform as close to ground level as is practical, with one or more discrete inlet ports (or a diffusive inlet) that span the width of the platform. One or more primary gas concentration measurements are performed with instrument 104.

Typically, these primary gas concentration measurements are originally recorded as concentration vs. time. Platform position vs. time data (e.g., using the Global Positioning System (GPS)) is combined with the concentration vs. time data to provide concentration vs. position data, schematically shown on FIG. 1b. Here a peak 112 and a background level 114 are shown.

The availability of concentration vs. position data enables automatic horizontal spatial scale analysis, which is useful for distinguishing gas leaks from background gas levels. In general, horizontal spatial scale analysis includes any analysis approach that makes use of concentration vs. platform position data for gas leak detection. A detailed example is given below. Note that simple thresholding (i.e., reporting a leak if measured concentration is greater than X, and not reporting a leak if the measured concentration is less than X, where X is some predetermined threshold value) is not an example of horizontal spatial scale analysis because no use is made of concentration vs. position data. Results of the automatic horizontal spatial scale analysis can be reported to an end user. Various approaches for this reporting are described below. One possibility is to provide a binary yes/no indication of whether or not a leak is present.

Horizontal Spatial Scale Analysis relies on the fact that nearby point sources vary rapidly with changing position as the platform moves, whereas distant sources vary more slowly, due to the larger spatial extent of the emission plume. In other words, narrow spikes in concentration just a few meters wide are generated very close to the platform. The narrow spatial extent is used to bias nearby sources in the leak identification process. There are several possible algorithms for performing horizontal spatial scale analysis, including but not limited to:

Peak finding and width analysis—the data can be analyzed using standard peak-location methods, and then each identified peak can be subsequently fit (using linear or nonlinear optimization) for center and width. The functional form used for this fitting step might be a Gaussian pulse (a Gaussian is the expected functional form taken by plumes propagating through the atmosphere), or the convolution of a Gaussian and the system response (which is typically a narrow Gaussian convolved with an exponential tail).

Spatial peak wavelet analysis—this algorithm uses a special model basis function (related to the discrete second derivative of the overall point-source system response function) that is parameterized by its width or spatial extent. This basis function set is convolved with the measurement data. The output wavelet analysis gives both the horizontal position and the effective width, which may be related via a gas plume model to the distance from the measurement to the emission source.

Preferably, the automatic horizontal spatial scale analysis is responsive to gas concentration peak half-widths in a detection range from about 1 m to about 50 m, and is substantially not responsive to gas concentration peak half-widths outside of the detection range. This spatial selectivity helps distinguish gas leaks from variations in background gas concentration. For example gas background concentration can vary significantly (e.g., by a factor of 2 or more), but this variation tends to be over a significantly larger spatial length scale than the above detection range. Note also that such large variations in background concentration significantly interfere with simple thresholding for finding gas leaks.

Primary gas concentration measurements are preferably performed rapidly (e.g., at a rate of 0.2 Hz or greater, more preferably 1 Hz or greater). This enables the concept of driving a vehicular platform at normal surface street speeds (e.g., 35 miles per hour) while accumulating useful concentration vs. position data. If the gas concentration measurements are too slow, spatial resolution of the data will undesirably be reduced. Preferably, platform position measurements are performed at least as rapidly as the primary gas concentration measurements.

Other significant attributes of the primary concentration measurement include:
1) The primary gas measurement analyte should be present in significant quantities for all leaks to be targeted by this method.
2) The typical background levels of this analyte in the environment where these measurements are made (e.g., urban) should be sufficiently low that the concentration change from the targeted leaks can be clearly distinguished from the local background signals at a distance of 10-300 meters.
3) For natural gas, methane is the most abundant constituent, but other hydrocarbons or other species (hydrogen sulfide or other odorants) are viable analytes for the primary concentration measurement.

Figure 2:
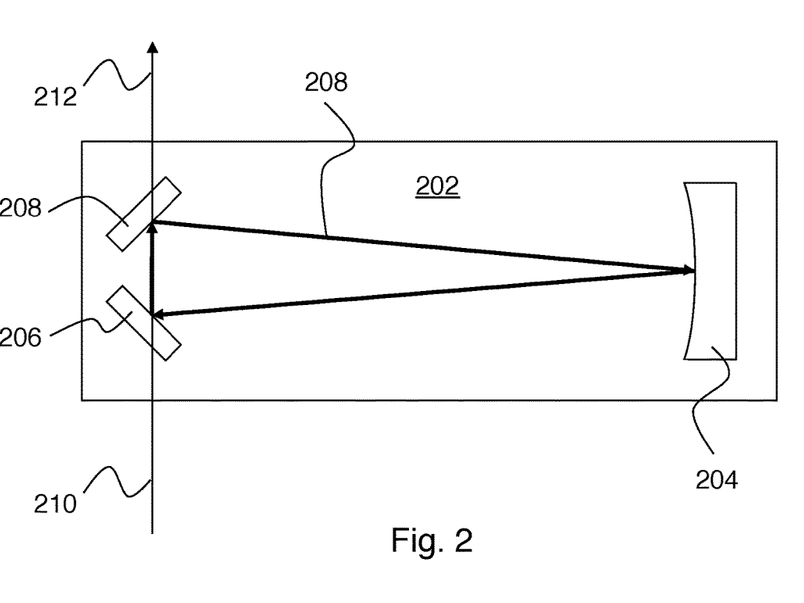
FIG. 2 schematically shows an exemplary optical absorption instrument suitable for use with embodiments of the invention.

The present invention does not depend critically on the gas detection technology employed. Any gas detection approach capable of providing rapid trace gas concentration measurements can be employed for the primary gas concentration measurements. One suitable gas detection approach is schematically shown on FIG. 2. Here the primary gas concentration measurements are optical absorption measurements made in a resonant optical cavity disposed in an instrument in the moving platform. More specifically, FIG. 2 shows an absorption cell 202 capable of holding a gas sample for analysis. Absorption cell 202 includes an optical cavity defined by mirrors 204, 206, and 208. This example shows a ring cavity with a uni-directional cavity mode 208 that propagates clockwise around the cavity. Any other resonant cavity geometry can be employed. Cavity absorption can be measured by comparing output light 212 to input light 210. Alternatively, cavity absorption can be measured by measuring the decay rate of optical radiation emitted from the cavity (i.e., cavity ring-down spectroscopy (CRDS)).

Horizontal spatial scale analysis can be combined with the use of tracers (isotope ratio tracers and/or chemical tracers) in order to provide leak source identification. Further details relating to tracers are provided in section B below.

Horizontal spatial scale analysis can also be combined with multi-point measurements and analysis as described in section C below. The resulting automatic transverse spatial scale analysis can provide a distance estimate to a leak source.

Although the primary gas concentration measurements are performed while the platform is moving, additional concentration measurements can be performed while the platform is stationary. Such stationary gas concentration measurements may be useful for checking background gas concentrations.

While real-time measurements are preferred, post analysis of more sparsely sampled data (e.g., via vacuum flask sampling and later analysis via gas chromatography or other methods) can also be a viable method for correctly identifying target emissions from other background sources.

Optionally, the system can include a source of atmospheric meteorological information, especially wind direction, but also wind speed or atmospheric stability class, either on-board the platform or at a nearby stationary location. 'Nearby' means close enough that the atmospheric conditions at the location of the platform are well-correlated to the stationary measurements.

Optionally, the system can include an on-board video camera and logging system that can be used to reject potential sources on the basis of the local imagery collected along with the concentration data. For example, a measured emissions spike could be discounted if a vehicle powered by natural gas passed nearby during the measurements.

The platform track should be as close to potential sources as possible. With decreasing distance to the emission source:
1) The primary concentration signal will increase, allowing for better confidence in source identification and/or more sensitive leak detection; 2) The effect of wind to hide signals or shift the measured location relative to the leak location is reduced; and 3) The spatial extent of the concentration signal from the leak becomes narrower, making it easier to distinguish from background signals and the plumes from more distant (or extended) sources, which have much more slowly varying signals.

Optionally, repeated measurements of a single location can be made to provide further confirmation (or rejection) of potential leaks.

Optionally, measurements can be made on different sides of the road or in different lanes to provide more precise localization of the leak source.

Optionally, the present approach can be used in conjunction with other conventional methods, such as visual inspection and/or measurements with handheld meters to detect emitted constituents, to further refine the results.

Optionally, measurements can be made at reduced speed, or parked at or near the source, to provide additional information on location and/or source attribution.

A2) Example

This section give a specific example of horizontal spatial scale analysis in connection with methane gas leak detection.

The methane concentration is measured initially as a function of time. It is combined with the output of the GPS receiver in order to obtain the methane concentration as a function of distance from some initial point. Interpolation can be used to sample the data on a regularly spaced collection of points.

The concentration of methane typically varies smoothly with position, for the most part being equal to the worldwide background level of 1.8 parts per million together with enhancements from large and relatively distant sources such as landfills and marshes. These enhancements can raise the background level by several parts per million. By contrast, a typical natural gas leak produces a plume of methane which is quite narrow in spatial extent. Although it varies with the atmospheric stability conditions, it is not until the plume has propagated more than 100 m that its half-width is of order 20 m in size.

The problem of detecting a gas leak by the spatial profile of the measured methane concentration thus involves:
1) Being insensitive to large-scale structure, which may be attributed to the background variations.
2) Detecting local enhancements in the methane concentration above the background consisting of peaks with half-widths in the approximate range of 1 m to 20 m.
3) Rejecting noise in the measurement due to instrumental imperfections.

The basic idea of this exemplary approach is to convolve the input concentration as a function of distance f(x) with a collection of Gaussian kernels $$g(x,w) = \exp(-x^2/2w)/\sqrt{2\pi w} \quad (1)$$

for a variety of scales specified by the parameter w (here w has dimensions of length squared). If we define L(x,w) to be the convolution of f(x) and g(x,w), the normalized second derivative $-w(\partial^2 L/\partial x^2)$ is sensitive to structures in f of spatial extent proportional to $\sqrt{w}$. For example, if f(x) is a Gaussian peak of half-width $\sigma$, i.e., $f(x) = \exp(-x^2/2\sigma^2)/(\sigma\sqrt{2\pi})$, we find that $$-w\left(\frac{\partial^2 L}{\partial x^2}\right) = \frac{w}{\sqrt{2\pi}} \left[\frac{w + \sigma^2 - x^2}{(w + \sigma^2)^{5/2}}\right] \exp\left[-\frac{x^2}{2(w + \sigma^2)}\right] \quad (2)$$

which has a maximum at $x=0$ and $w=2\sigma^2$. The value of the maximum is about 0.385 times the amplitude of the original peak in f. Away from the peak, this falls smoothly to zero.

The basis of the algorithm is to calculate the surface $-w(\partial^2 L/\partial x^2)$ and to examine the result for local maxima in both x and w. For each maximum $(\hat{x},\hat{w})$ the position $x_0$ and half-width $w_0$ of the corresponding peak are reported as $x_0=\hat{x}$ and $w_0=\sqrt{\hat{w}/2}$, and the peak amplitude is scaled from the value of the surface at the maximum. Only a range of w is considered, corresponding to a range of peak half-widths of typically 1 m to 20 m that correspond to plume dimensions seen in leak detection.

Several mathematical properties allow for the more convenient calculation of the above space-scale surface. Since the Gaussian kernels satisfy $\partial g/\partial w = \frac{1}{2}\partial^2 g/\partial x^2$, it is possible to compute the surface as the convolution of $-2w(\partial g/\partial w)$ and the input function f(x). A finite number of values of w are used in practice, spaced geometrically, namely $w \in \{w_1, w_2, \ldots w_n\}$ where $w_i = \lambda^{(i-1)} w_1$ for some $\lambda > 1$. The partial derivative of g with respect to w can also be approximated by a finite difference, and the convolutions computed as discrete summations.

It is possible to organize the computation of the space-scale surface in a pipelined manner, so that a stream of samples of f(x) is used as input. The convolutions can be evaluated lazily so that at any stage, only enough samples of the surface are produced as are needed to determine whether a point on the surface is a local maximum. Once that determination has taken place, samples which are no longer needed are discarded, so that the entire calculation can take place in near real time in a limited amount of memory.

Having obtained the locations, amplitudes and widths of candidate peaks, an additional filtering step can be applied which selects amplitudes above a certain threshold (or within a certain range). As described in greater detail in section D below, the remaining peaks can be displayed as leak indications, using icons whose sizes indicate the amplitude of the peak, and whose positions on a map indicate where along the path the peak was located.

B) Tracers

We have found that source identification can be performed using isotopic ratio measurements. For example, methane isotopic ratios ($\delta D$ of $CH_4$ (0/00) relative to Vienna standard mean ocean water (VSMOW), and $\delta^{13}C$ of $CH_4$ (0/00) relative to Vienna Pee Dee Belemnite (VPDB)) fall in characteristic ranges depending on the source of the methane. For near-surface microbial gas (e.g., marsh gas, landfill gas), these ranges are about $-350 < \delta D < -260$ and $-63 < \delta^{13}C < -40$. For sub-surface microbial gas (e.g., deep sea sediments and drift gas), these ranges are about $-250 < \delta D < -170$ and $-90 < \delta^{13}C < -60$. For thermogenic gas (e.g., natural gas and coalbed gas), these ranges are about $-250 < \delta D < -100$ and $-57 < \delta^{13}C < -28$. Since these ranges basically do not overlap, isotope ratio measurements can be used to provide source identification for methane. It is expected that isotope ratio source identification is applicable in general for leak measurements of any gas.

Thus, a method according to this aspect of the invention starts with primary gas concentration measurements from a moving platform as described above (horizontal spatial scale analysis can be performed or omitted from the above-described methods). One or more secondary isotope ratio measurements from the moving platform are also performed from the moving platform. The secondary isotope ratio measurements are used to provide source identification, while the primary gas concentration measurements are used to determine presence/absence of a gas leak. These results are provided to an end user.

Optionally, chemical tracer analysis can be performed in addition to the isotope ratio analysis for source identification. For example, natural gas tagged with mercaptans can use the mercaptans as a chemical tracer to distinguish vs. other sources of natural gas, in combination with the isotopic ratio source identification.

Significant attributes of the tracer measurements (i.e., chemical and/or isotope ratio) are as follows:
1) The tracer should be present in the emitted gas in a known, constant ratio to the primary constituent for all likely leaks within a target measurement area. This ratio represents a 'signature' of the target source.
2) The ratio signature of the target emission source should be different and distinguishable from other common sources of the primary constituent that can be found in the target measurement area.
3) The ratio signature of the target emission source should also be different from the ratio signature for the ambient background.

For example, for the case of methane as the primary concentration measurement, other common sources of methane in an urban environment are sewer systems, landfills, petrochemical processing facilities, or other industrial activity. An example of a useful tracer for methane is the stable isotope ratio of carbon ($^{13}C/^{12}C$) in the methane sample. Natural gas is an example of a petrogenic source of methane, which has a different stable isotope ratio than the biogenic gas emitted by from the sewer system, storm drains, or landfills, for example.

Other candidate tracer species include but are not limited to the hydrogen stable isotope ratio $^2H/^1H$, hydrogen sulfide or other odorants in the natural gas; or ethane, propane, or other hydrocarbons.

Optionally, multiple tracers give additional dimensionality, allowing for even more effective methods of distinguishing target sources from other sources of the primary constituent.

One application of multiple tracer measurements is to distinguish between three sources of methane that are important in practice: natural gas, biogenic methane (e.g., landfill gas), and methane from vehicle exhaust.

Methane is emitted in significant quantities from gasoline or diesel powered vehicles. Methane is a product of incomplete combustion, so emissions are especially large for those vehicles that do not have a catalytic converter. During a survey, if the leak survey vehicle passes through the exhaust plume of another vehicle, the methane present in the exhaust plume could be incorrectly interpreted as a natural gas leak or as emissions from a landfill. Because the $\delta^{13}C$ signature of a vehicle exhaust plume is not necessarily different from that of natural gas or landfill gas, the source of a methane signal cannot be distinguished using a single secondary carbon isotope ratio tracer. Adding an additional tracer measurement that can uniquely identify a vehicle exhaust plume would permit the system to distinguish between each of the three source categories of interest for this application. Possible additional tracer molecules that allow one to distinguish vehicle exhaust from biogenic sources and natural gas include but are not limited to carbon dioxide ($CO_2$), nitrous oxide ($N_2O$), ethane ($C_2H_6$), carbon monoxide ($CO$), ethylene ($C_2H_4$), acetylene ($C_2H_2$), and nitric oxide ($NO_2$). The last four tracers are preferred choices, because a) they are coemitted with methane during incomplete fuel combustion, b) there are few other sources of these gases in the environment where natural gas leaks may be present, and c) these gases are not present in natural gas or landfill gas.

In some instances, measuring the simple presence (or absence) of a tracer species is sufficient to distinguish between two or more possible source types. In other instances where the tracer species is present in both possible source type plumes but in differing amounts, it is advantageous to consider a tracer ratio, which is defined as the ratio of the tracer species concentration to the primary gas species concentration. Finally, in instances where the tracer species and/or the primary gas species are present in the ambient air background in which the plume measurements are made, a background-corrected tracer ratio can be used, which is defined as the difference between the tracer species concentration in the plume ($T_{plume}$) and the tracer species concentration in the background ($T_{background}$), divided by the same quantity calculated for the primary gas species, or $$r = \frac{T_{plume} - T_{background}}{C_{plume} - C_{background}}$$

Here $C_{plume}$ is the primary gas species concentration in the plume and $C_{background}$ is the primary gas species concentration in the background.

Figure 9:
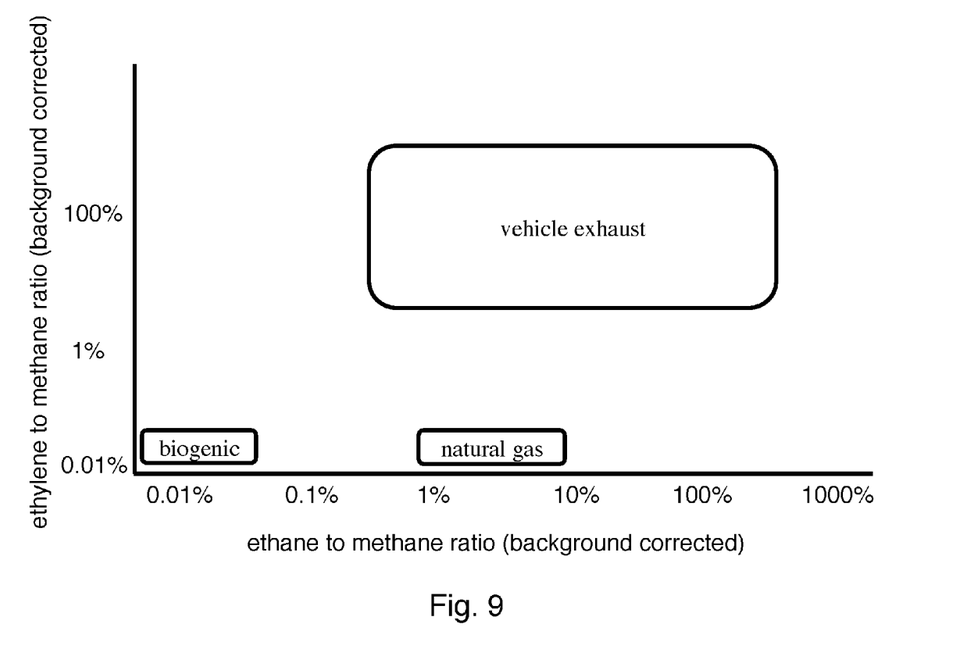
FIG. 9 schematically shows identification of three methane source types using two chemical species tracers.
Figure 10:
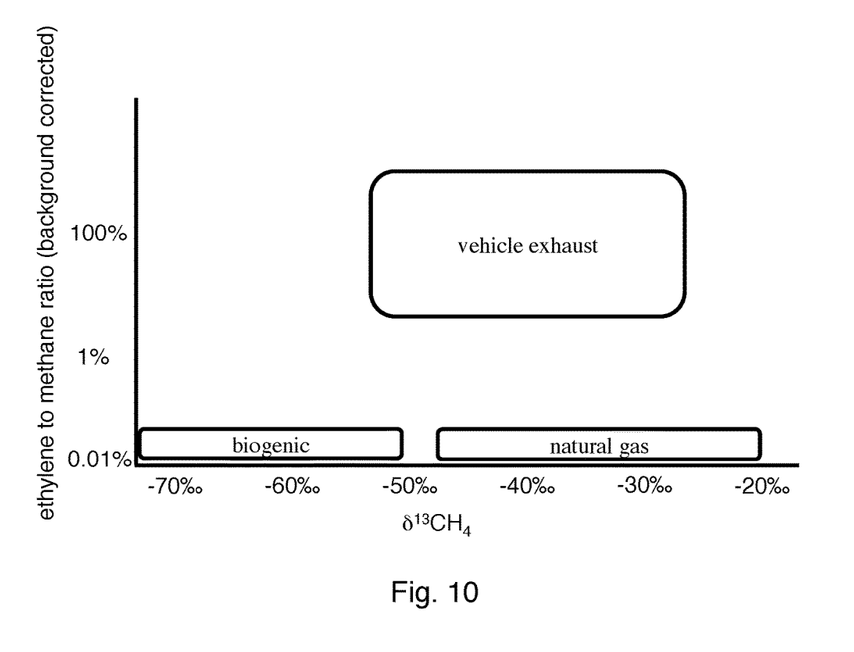
FIG. 10 schematically shows identification of three methane source types using an isotope ratio tracer combined with a chemical species tracer.

FIGS. 9-10 schematically show multi-tracer source identification. The example of FIG. 9 schematically shows identification of three methane source types using two chemical species tracers. In this example, vehicle exhaust and natural gas cannot be distinguished with an ethane/methane background-corrected concentration ratio tracer measurement, while ethylene/methane background-corrected concentration ratio can distinguish between these two sources of methane. However the ethylene measurements cannot distinguish between biogenic methane and methane from natural gas, while the ethane measurements can distinguish between these two sources. Thus two different tracer measurements can be needed to provide sufficient source identification in practical cases.

The example of FIG. 10 schematically shows identification of three methane source types using a chemical species tracer and an isotope ratio tracer. In this example, vehicle exhaust and natural gas cannot be distinguished with a carbon-13 isotope ratio tracer measurement, while ethylene/methane background-corrected concentration ratio can distinguish between these two sources of methane. However the ethylene measurements cannot distinguish between biogenic methane and methane from natural gas, while the carbon-13 isotope ratio measurements can distinguish between these two sources. This is another example of two different tracer measurements being needed to provide sufficient source identification in practice.

Figure 3A:
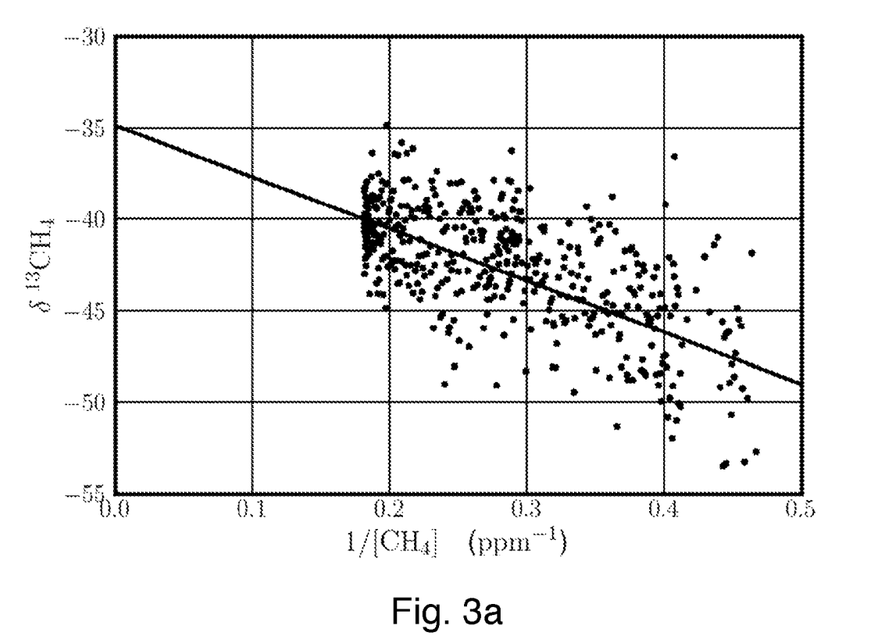
FIGS. 3a-b show isotopic analysis results from an embodiment of the invention.
Figure 3B:
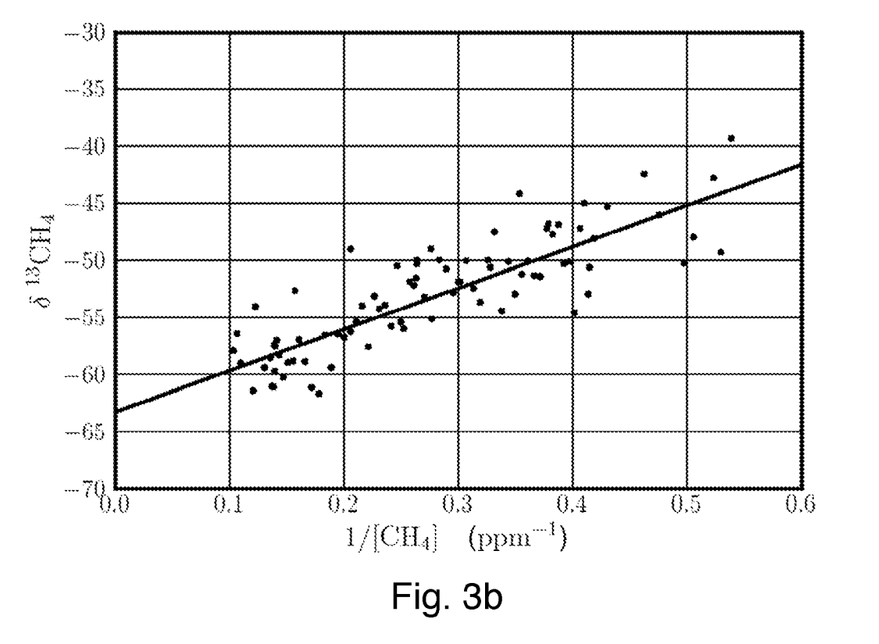

Any approach for performing the isotope ratio analysis can be employed. One preferred approach is to perform source identification according to the y-intercept of a linear fit of isotope ratio vs. inverse concentration (known as a Keeling plot). FIGS. 3a-b show examples of such plots. The example of FIG. 3a shows a typical signal for a leak detection (y intercept differs from background level). The example of FIG. 3b shows a typical background signal (y intercept same as background level).

The basic principles of a Keeling plot analysis are as follows. For a single tracer, this ratio will vary from the background value in ambient air to a value that approaches, but does not reach, the ratio found in the pure emission, due to the fact that the observed ratio is due to a mixture of background gas and emissions. An analysis called a Keeling plot (developed by Charles Keeling for the analysis of carbon 13 present in atmospheric carbon dioxide) can be used to clearly identify background and source, by plotting the tracer ratio as a function of the inverse of the observed primary concentration. The intercept of this graph is the tracer ratio of the emission source. If this value can be distinguished from other possible sources, then an unambiguous source determination can be made. In this instance, 'distinguished from' means that the intercept determined from the plot does not differ from the expected source signature in a statistically significant manner. For multiple tracers, the Keeling method can be extended to multiple tracer ratios.

The Keeling methods are best applied when the tracer measurements can be made in real time. For flask type measurements where the number of data points are more limited, the Keeling method can still be applied for source determination, as long as care as taken to collect flask samples both at or near the peak, and on the baseline nearby, where the concentration levels have returned to ambient but not so far away that other sources of the primary concentration or the tracer are influencing the results.

Alternatively, an approach by J. B. Miller and P. P. Tans (Tellus, 55B, 207-214, hereby incorporated by reference in its entirety) may be employed, in which the tracer concentration is plotted as a function of the primary concentration and a linear regression is performed on these data. The slope of the line of best fit is used to estimate the tracer ratio of the gas leak. An advantage of this method is that the uncertainty in the tracer concentration often does not vary with the primary concentration, allowing the use of a simpler unweighted linear regression algorithm.

Figure 4:
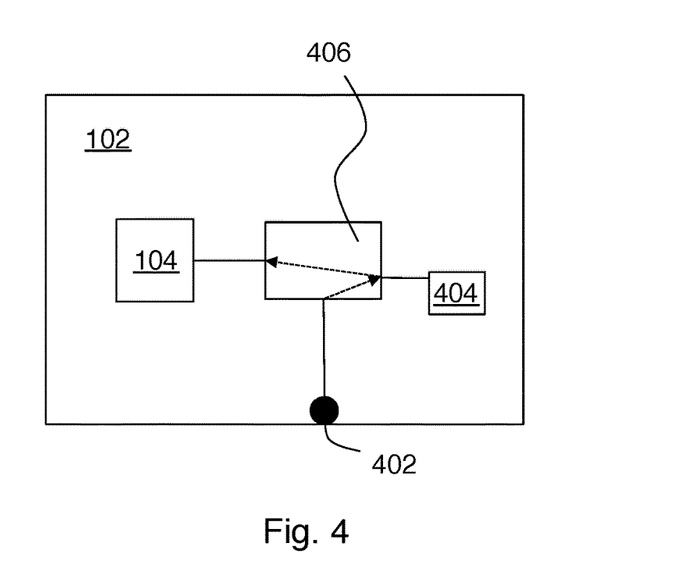
FIG. 4 shows a gas handling approach suitable for use in connection with isotope ratio measurements.

In some cases, a gas handling system can be employed in connection with the secondary isotope ratio measurements. For example, a gas handling system can be used to acquire one or more samples and to provide the acquired samples to an off-line isotope ratio measuring instrument. Here off-line indicates that the isotope ratio measurements are typically significantly slower than the primary gas concentration measurements as described above. Thus, the isotope ratio measurement are off-line with respect to the time scale of the primary concentration measurements. However, the isotope ratio measurement instrument is preferably disposed on the moving platform. Acquired isotope ratio samples can be analyzed on-board. FIG. 4 shows an example. Here a gas handling system 406 stores a sample acquired at inlet 402 in chamber 404, and is capable of providing the contents of chamber 404 to instrument 104 (here instrument 104 is an isotope ratio instrument).

Any approach for performing secondary isotope ratio measurements can be employed. If chemical tracers are measured as well, any approach for such tracer measurements can be employed. Preferably, optical absorption spectroscopy as described above is employed. Stationary measurements can be used in addition to the primary gas concentration measurements, as described above.

Secondary isotope ratio measurements can be combined with multi-point measurements and analysis as described in section C below. The resulting automatic transverse spatial scale analysis can provide a distance estimate to a leak source.

C) Multi-Point Measurements for Distance Estimation

Figure 5A:
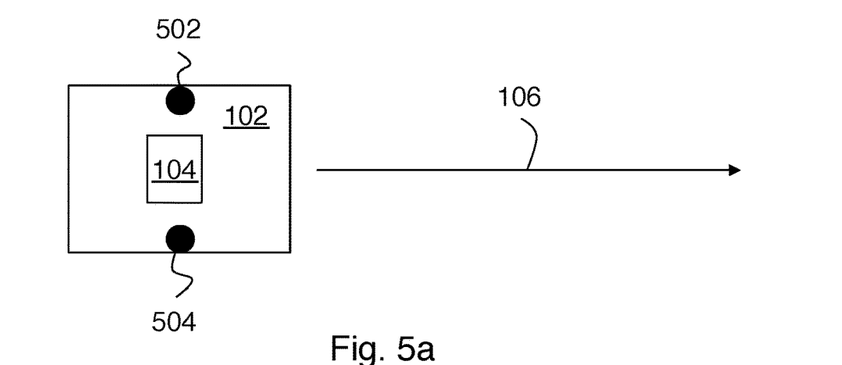
FIGS. 5a-c schematically show multi-point measurements according to embodiments of the invention.
Figure 5B:
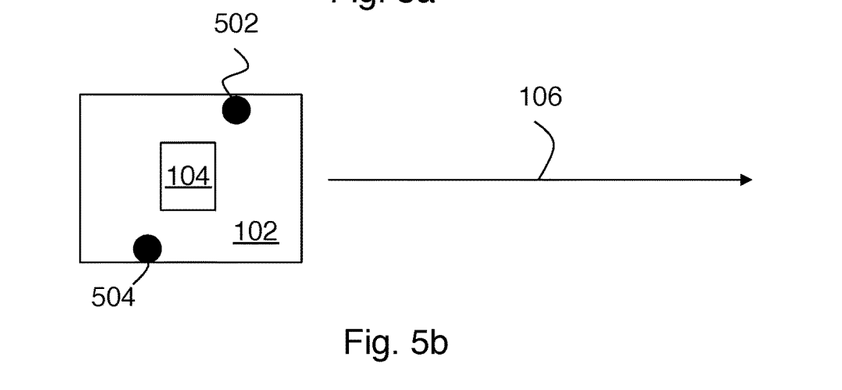
Figure 5C:
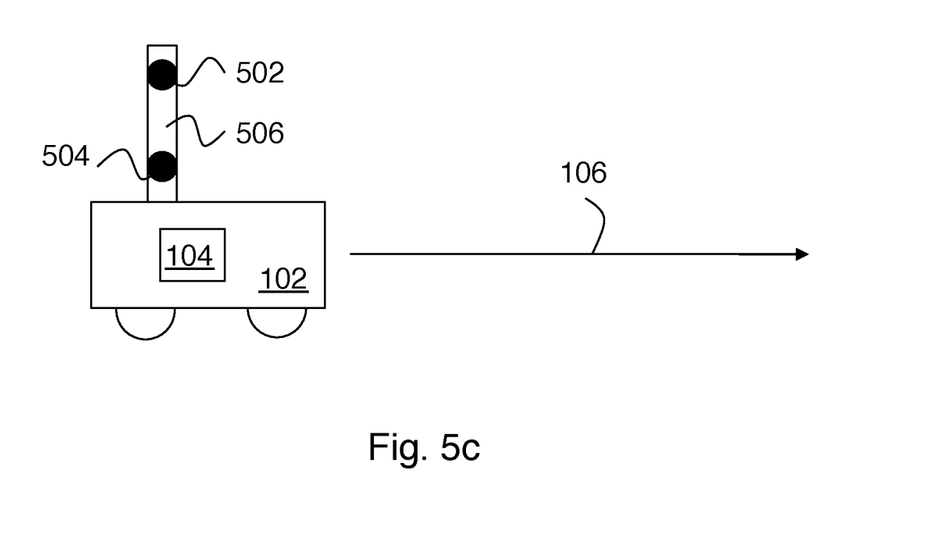

We have found that multi-point measurements can be useful for providing an estimate of distance to the leak source. Here, a multi-point measurement is any measurement from two or more points on the moving platform that are transversely separated from each other. FIGS. 5a-c show example of transverse separation. Let z be the direction of platform travel, y be the vertical direction and x be perpendicular to y and z. FIG. 5a shows transversely separated measurement points 502 and 504 where the separation is entirely in the x direction. FIG. 5b shows transversely separated measurement points 502 and 504 where the separation is partly in the x direction and partly in the z direction. Points 502 and 504 on FIG. 5b are transversely separated because there is a non-zero separation in the x direction. FIG. 5c shows transversely separated measurement points 502 and 504 where the separation is entirely in the y direction. Here the measurement points are disposed on a mast 506.

A method according to this aspect of the invention starts with primary gas concentration measurements from a moving platform as described above (horizontal spatial scale analysis can be performed or omitted from the above-described methods). The multi-point measurements are used to provide a distance estimate. More specifically, a distance between a platform measurement position and a leak source location is estimated, where the platform measurement position is the platform position at the time the relevant measurements were performed. Automatic spatial scale analysis of the multi-point measurements is used to provide this distance estimate. Results, including the distance estimate, can be provided to an end user in various ways. Preferably, the measurement points are separated from each other vertically (e.g., as in the example of FIG. 5c).

The spatial scale analysis can include providing a gas leak plume model and inverting this model to determine a source distance from a measured concentration gradient. Note that this measured concentration gradient can be determined from multi-point measurements as considered herein. Real-time atmospheric data can be included in the gas plume model.

Figure 6A:
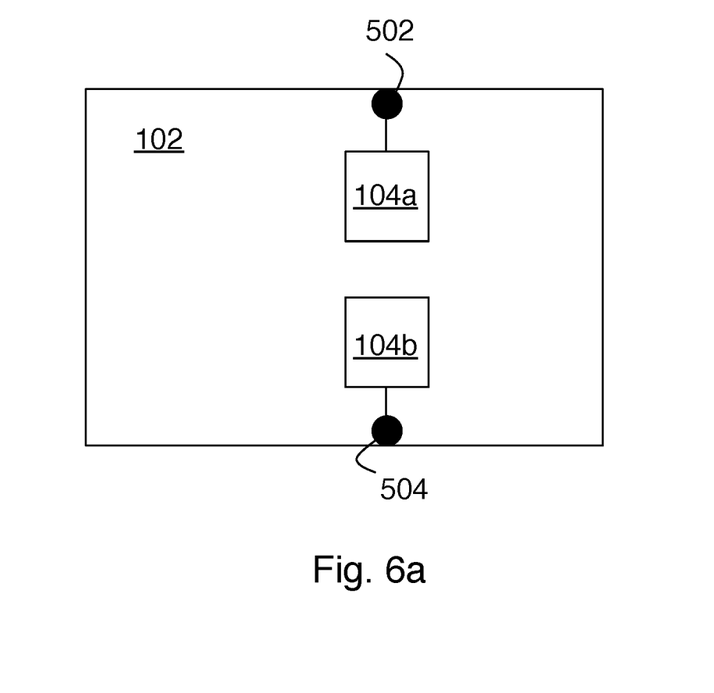
FIGS. 6a-c schematically show some gas handling approaches suitable for multi-point measurements.
Figure 6B:
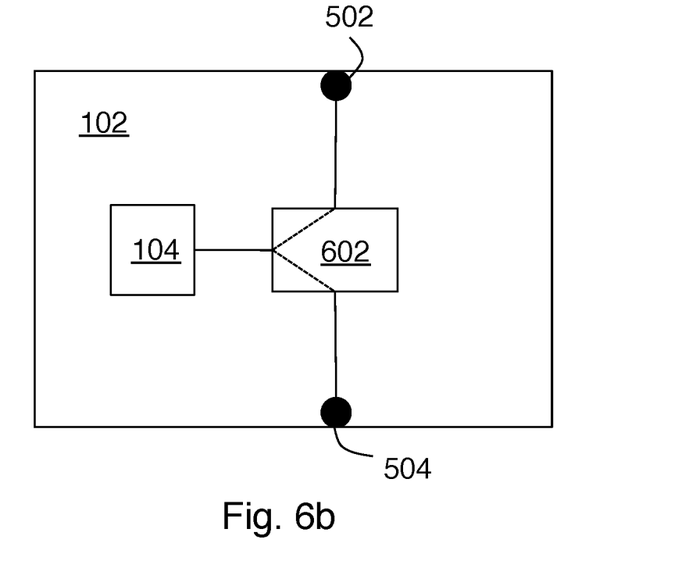
Figure 6C:
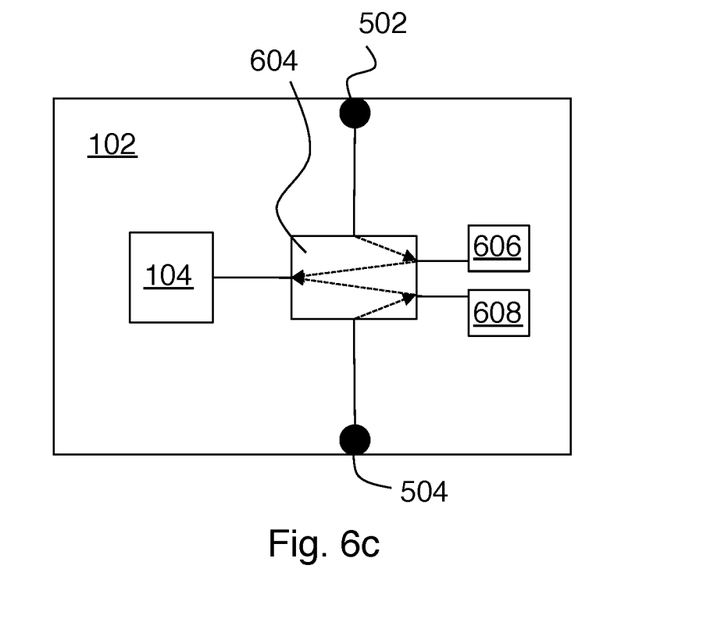

Various gas handling approaches can be employed in connection with multi-point measurements. The underlying requirement is to obtain simultaneous or nearly simultaneous (i.e., preferably within about 5 seconds, more preferably within about 1 second) measurements. FIGS. 6a-c show examples of various two-point measurements. All of these approaches can be extended to measurements at any number of transversely separated points. The example of FIG. 6a shows two instruments 104a and 104b having separated inlets 502 and 504. This can clearly provide simultaneous measurements, but has the disadvantage of increasing cost by duplicating the measurement instrument. The example of FIG. 6b shows a single instrument 104 connected to inlets 502 and 504 via a switch 602. If the switch and instrument are sufficiently fast, this approach can provide nearly simultaneous measurements at the inlets. The example of FIG. 6c shows a gas handling system 604 having separated inlets 502 and 504 that is capable of providing simultaneously or nearly simultaneously acquired samples to a single instrument in sequence. For example, samples acquired at inlets 502 and 504 can be stored in chambers 606 and 608 respectively, and provided to instrument 104 in sequence. The time difference between analysis of chamber 606 and chamber 608 is not important.

Preferably, primary gas concentration measurements are performed with optical absorption spectroscopy as described above. Stationary gas concentration measurements as described above can also be employed.

C2) Multi-point Example

We consider the following example of using multiple vertical measurements of a plume to quantify the distance from the measurement to the upwind source location. One well-validated physical model for a plume, developed by Gifford in 1959, is to model the plume as a Gaussian distribution in the spatial dimensions transverse to the wind direction, or (for a ground level source)

$$C(x, y, z) = \frac{Q}{\pi V \sigma_y \sigma_z} \exp(y^2/2\sigma_y^2 - z^2/2\sigma_z^2) \quad (3)$$

As expected, the dimensions of the Gaussian distribution horizontally and vertically (i.e., $\sigma_y$ and $\sigma_z$ respectively) increase with increasing distance, and the amount they increase can be estimated from measurements of wind speed, solar irradiation, ground albedo, humidity, and terrain and obstacles, all of which influence the turbulent mixing of the atmosphere. However, if one is willing to tolerate somewhat more uncertainty in the distance estimation, the turbulent mixing of the atmosphere can be estimated simply from the wind speed, the time of day, and the degree of cloudiness, all of which are parameters that are available either on the platform or from public weather databases in real time. Using these available data, estimates of the Gaussian width parameters can be estimated (e.g., by using the Pasquill-Gifford-Turner turbulence typing scheme, or modified versions of this scheme). For example, one possible functional form for $\sigma_y$ and $\sigma_z$ is $\sigma = ax/\sqrt{1+bx}$, where a and b are fitting parameters and x is distance along the plume axis. Separate fits can be performed for the y and z directions, or the same fit can be used for both directions.

The multi-point vertical measurement can be used to estimate the vertical Gaussian width. The horizontal width can also be estimated from horizontal spatial scale analysis, but the vertical analysis has the advantage that the vertical extent of the plume is not as strongly distorted by the motion of the platforms and other nearby platforms as is the horizontal dimension, where the plume can be carried along horizontally by the motion of a platform.

Given the estimate of the vertical Gaussian width, available look up tables can be used to determine the distance from the source given the width and the available information about the turbulent mixing of the atmosphere. Even without any atmospheric measurements whatsoever, a crude distance estimate can be determined (such as on-road, near-road, or far), which would provide valuable additional information to an inspector searching for the source of the emissions.

Other forms of multi-point analysis can be performed, as an alternative to using a plume model. For example, for on road sources, a measurement point at or near the road surface (e.g., within 25 cm) which is close to the emission source will see a dramatically different concentration than a measurement point on a 2-3 meter mast. In this situation, the Gaussian plume model breaks down, and a threshold analysis such as (delta peak height)/(average peak height)>t (where the threshold t is the order of 0.5) can unambiguously identify such sources as local (e.g., on-road).

D) User Interface

Figure 7:
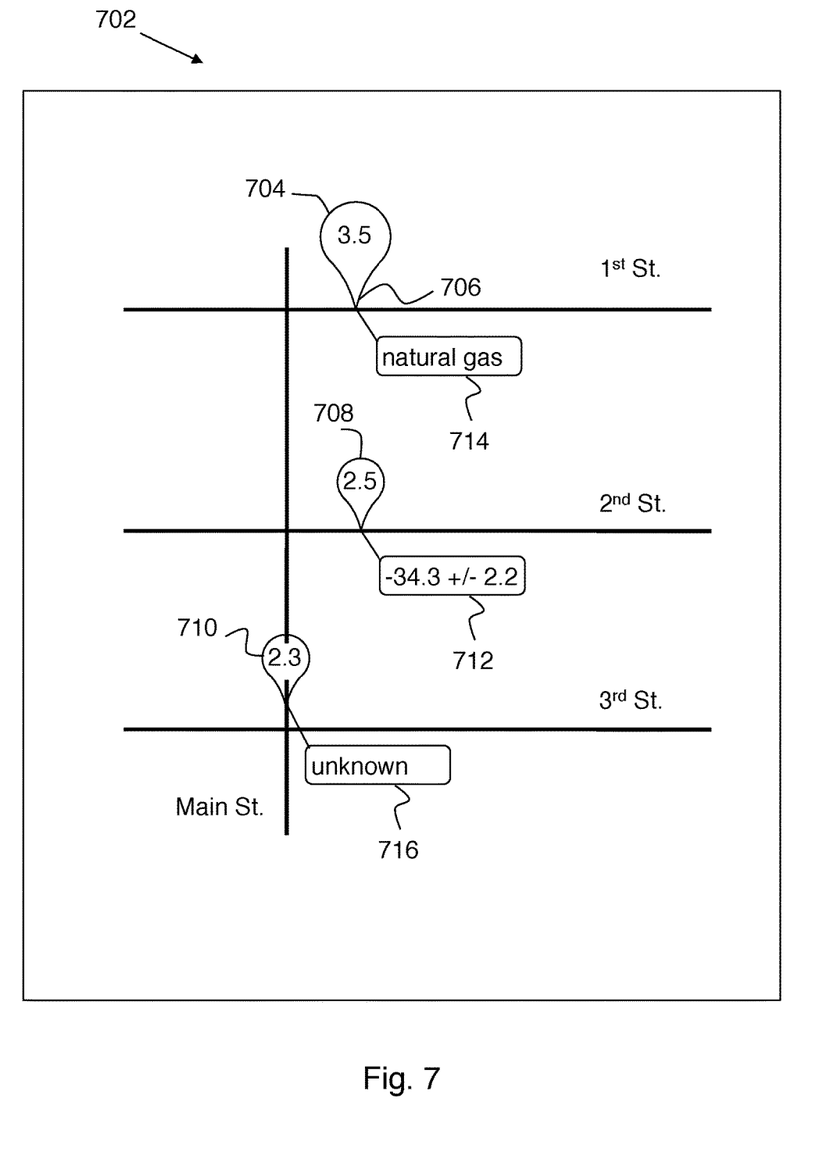
FIG. 7 shows an exemplary user interface display relating to embodiments of the invention.

FIG. 7 shows an exemplary user interface relating to embodiments of the invention. Here a map display 302 has leak figures (e.g., 704, 708, 710) superposed on it. The leak figures include pointers (e.g., 706) that show the location of detected leaks (i.e., platform positions at which the corresponding leak concentrations were measured). The figure size can be scaled according to quantities such as the peak amplitude (i.e., the amount by which the peak concentration exceeds the local background), the peak concentration, or the measured spatial width of the peak. Numerical parameters (such as the amplitude, concentration, width, or a severity rank of the leak within some defined region, etc.) can be displayed inside the leak figures. If isotope ratio measurements are performed, they can also be shown on the display (e.g., 712). If qualitative source identification is automatically performed based on the isotopic ratio measurements, then the qualitative results can be shown on the map (e.g., 714 and 716). The leak figures can have any shape. The pointers on the leak figures can have any shape.

E) Automatic Qualitative Source Attribution

Optionally, the results of the isotope ratio analysis may be automatically mapped to possible analysis outcomes representing statements about likely source attribution. The results of the isotopic analysis to be used as inputs to the mapping include, at minimum, the best estimate of the isotopic ratio as determined, for example, from the Keeling analysis. Optionally the uncertainty in the measurement may also be used as input. Possible analysis results, or outputs, or outcomes of the mapping could include, "natural gas", "not natural gas", "biogenic methane", "unknown", or "out of range" (to represent a faulty measurement). These categories make it possible to build and apply simple models that take into account our prior knowledge about the frequency of the various different measurement or analysis outcomes for a given source type (e.g., as described in section B above). For example, the outcome of "unknown" could be used to denote that the source attribution is ambiguous given the measurement result.

Figure 8:
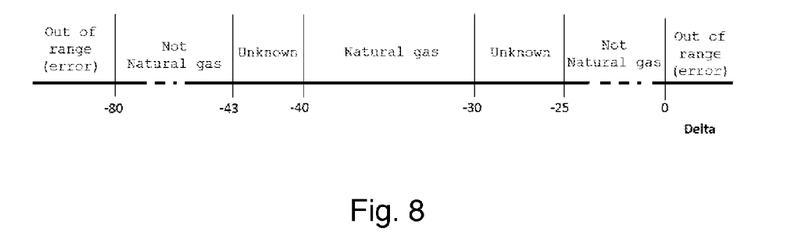
FIG. 8 shows an exemplary assignment of qualitative results to isotopic ratio measurement results.

Optionally, the uncertainty in the measured isotopic ratio may be taken into account in the source attribution model. Taking account of the uncertainty allows for a simple and automatic way for the quality of measurement to be assessed, and a more meaningful result to be returned to the user. For example, one approach would be to assign a result of "unknown" to any measurement whose measurement uncertainty exceeds a predetermined threshold (which might range between 1 and 5 parts per thousand, being preferably 2 parts per thousand). Alternatively, one may require that any measurement whose 1-sigma uncertainty band overlaps any boundaries between two attribution results map to a result of "unknown". One possible mapping of delta values that we have found to result in reliable source attribution when using either of the two methods described above is shown on FIG. 8. For example, if using the mapping of FIG. 8, a result of −39+/−2 would result in "natural gas" if using the attribution model taking into account only the delta value. When using a model that requires the entire 1-sigma uncertainty band to lay within a single band, this measurement would result in the attribution result "unknown" even though the central value of measurement falls within the range of "natural gas".

Optionally, a measurement may be mapped to "out of range" if its uncertainty exceeds a predetermined value that typically indicates a failure of the measurement, or if other measurement quality selection criteria are not satisfied. For example, quality criteria may require include a minimum number of points to be fit in the Keeling analysis, or a minimum range of inverse-concentration values be present.

Automatic source attribution may also be accomplished by using a likelihood ratio test. Let us assume there are N possible source-type hypotheses, $H_i$ with $1 \le i \le N$, and that the frequency with which a particular isotopic analysis result, E, is obtained as a result of a measurement of source type $H_i$ is described by a probability density function $P(E|H_i)$. Then the source hypothesis $H_j$ is considered true if $$\frac{P(E\mid H_j)}{P(E\mid H_i)} > R, \quad \text{for all } i \neq j, P(E\mid H_i) > 0 \qquad (4)$$

where R is a predetermined threshold value ranging from about 2 to about 100, preferably chosen to be about 10, meaning that source type hypothesis $H_j$ is at least 10 times more likely than any other hypothesis. If no source type hypothesis satisfies the condition of Equation 1, a result of "unknown" is returned.

In another embodiment, the probability that the source hypothesis $H_j$ is true given the analysis result E, $P(H_j|E)$, is computed using Bayes theorem:

$$P(H_j\mid E) = \frac{P(E\mid H_j)P(H_j)}{\sum_i (E\mid H_i)P(H_i)} \qquad (5)$$

where $P(H_i)$ is the prior probability of hypothesis $H_i$. If we assume that all hypotheses are equally probable, then $$P(H_i) = \frac{1}{N} \text{ for } 1 \leq i \leq N.$$

The qualitative source attribution result corresponding to $H_j$ is returned if the posterior probability, $P(H_j|E)$, exceeds a predetermined threshold, and a result of "unknown" is returned otherwise. The value of the threshold may be chosen to be between 0.5 and 1, with a choice of about 0.9 or greater in preferred embodiments.

According to another embodiment, the above technique may be extended to include the results of two or more measurements of the same source using Bayesian updating, where the distributions describing probabilities of the hypotheses are updated such that $P_{k+1}(H_j)=P(H_j|E_1, E_2, \ldots, E_k)$ after the kth measurement. An attribution result of "unknown" is returned until the probability of one of the hypotheses exceeds a threshold between 0.5 and 1, with a choice of about 0.9 or greater in preferred embodiments.

The probability distributions describing the frequencies with which isotopic ratio results are obtained from a particular source type may depend on the geographical region where the measurements are made. Some distribution systems deliver natural gas that is a mixture of gas from multiple geological basins or other sources. It is possible that the isotopic signature of the mixed gas can vary in time as the relative contribution from different sources is changed. If one has a priori knowledge of the composition of the gas being distributed, this information can be incorporated into the source attribution model by appropriately changing the likelihood function describing the frequency with which a given measurement result is obtained when measuring the mixed-source gas.

The invention claimed is:

1. A method of gas leak detection and localization, the method comprising:
    performing one or more primary gas concentration measurements of a target gas species from a moving platform that proceeds along at least one platform track disposed near one or more potential gas leak locations;
    performing two or more secondary tracer measurements of the target gas species from the moving platform as it proceeds along the at least one platform track;
    automatically determining whether or not a gas leak is present at the potential gas leak locations based on the primary gas concentration measurements and the two or more secondary tracer measurements, wherein the secondary tracer measurements provide source identification for detected leaks of the target gas species into three or more distinct categories; and
    providing a leak indication at the potential gas leak locations to an end user.

2. The method of claim 1, wherein the performing two or more secondary tracer measurements comprises using a gas handling system to acquire one or more samples and providing acquired samples to an off-line tracer measuring instrument.

3. The method of claim 1, wherein the secondary tracer measurements are optical absorption measurements made in a resonant optical cavity disposed in an instrument in the moving platform.

4. The method of claim 1, further comprising
    performing one or more of the primary gas concentration measurements at two or more transversely separated locations on the moving platform as it proceeds along the at least one platform track;
    performing an automatic transverse spatial scale analysis of the primary gas concentration measurements;
    wherein the automatically determining whether or not a gas leak is present at the potential gas leak locations is also based on the automatic transverse spatial scale analysis.

5. The method of claim 1, further comprising performing one or more stationary gas concentration measurements when the platform is stationary.

6. The method of claim 1,
    wherein one of the two or more secondary tracer measurements is selected from the group consisting of: ethane concentration, ethane/methane concentration ratio, ethane/methane background-corrected concentration ratio, hydrogen stable isotope ratio and carbon stable isotope ratio; and
    wherein another of the two or more secondary tracer measurements is selected from the group consisting of: ethylene concentration, acetylene concentration, carbon monoxide concentration, nitrous oxide concentration, nitrogen dioxide concentration, ethylene/methane concentration ratio, acetylene/methane concentration ratio, carbon monoxide/methane concentration ratio, nitrous oxide/methane concentration ratio, nitrogen dioxide/methane concentration ratio, ethylene/methane background-corrected concentration ratio, acetylene/methane background-corrected concentration ratio, carbon monoxide/methane background-corrected concentration ratio, nitrous oxide/methane background-corrected concentration ratio, and nitrogen dioxide/methane background-corrected concentration ratio.

7. The method of claim 6, wherein $T_{plume}$ is a tracer species concentration in a gas plume, wherein $T_{background}$ is a background concentration of the tracer species, wherein $C_{plume}$ is a primary gas species concentration in the gas plume, wherein $C_{background}$ is a background concentration of the primary gas species, and wherein the background-corrected concentration ratio r is given by $$r = \frac{T_{plume} - T_{background}}{C_{plume} - C_{background}}.$$

8. The method of claim 1, wherein the leak indication is a binary yes/no indication of whether or not a leak is present.

9. The method of claim 1, further comprising providing a display showing a map with leak figures superposed on the map to show detected leaks, wherein the leak figures include pointers showing the locations of detected leaks.

10. The method of claim 9, wherein sizes of the leak figures are scaled with the measured primary gas concentration.

11. The method of claim 9, wherein sizes of the leak figures are scaled with a difference between the measured primary gas concentration and a local background level.

12. The method of claim 9, wherein distinct colors of the leak figures correspond to the three or more distinct categories.

13. The method of claim 9, further comprising superposing tracer measurements on the map corresponding to one or more of the detected leaks.

14. The method of claim 1, wherein the secondary tracer measurements comprise one or more concentration measurements of tracer species.

15. The method of claim 1, wherein the secondary tracer measurements comprise one or more concentration ratio measurements of tracer species concentration relative to the primary gas concentration measurements.

16. The method of claim 1, wherein the secondary tracer measurements comprise one or more background-corrected concentration ratio measurements of tracer species concentration relative to the primary gas concentration measurements.

17. The method of claim 16, wherein $T_{plume}$ is a tracer species concentration in a gas plume, wherein $T_{background}$ is a background concentration of the tracer species, wherein $C_{plume}$ is a primary gas species concentration in the gas plume, wherein $C_{background}$ is a background concentration of the primary gas species, and wherein the background-corrected concentration ratio r is given by $$r = \frac{T_{plume} - T_{background}}{C_{plume} - C_{background}}.$$

18. The method of claim 1, wherein the secondary tracer measurements comprise one or more isotope ratio measurements of tracer species.

* * * * *